United States Patent [19]

Hagen et al.

[11] E Patent Number: Re. 32,154

[45] Reissued Date of Patent: May 20, 1986

[54] PRODUCTION OF 2-(O-ALKYLTHIOPHENYL)-1,3-DIAZOCYCLOALKENE HYDROHALIDES

[75] Inventors: Helmut Hagen, Frankenthal; August Amann, Ludwigshafen; Hubert Giertz, Limburgerhof, all of Fed. Rep. of Germany

[73] Assignee: BASF Aktiengesellschaft, Fed. Rep. of Germany

[21] Appl. No.: 237,961

[22] Filed: Feb. 25, 1981

Related U.S. Patent Documents

Reissue of:

[64] Patent No.: 4,122,263
Issued: Oct. 24, 1978
Appl. No.: 807,673
Filed: Jun. 17, 1977

U.S. Applications:

[63] Continuation-in-part of Ser. No. 349,915, Apr. 11, 1973, abandoned.

[30] Foreign Application Priority Data

Apr. 22, 1972 [DE] Fed. Rep. of Germany ..... 2219841

[51] Int. Cl.[4] ..... C07D 239/26

[52] U.S. Cl. ..... 544/114; 544/122; 544/139; 544/295; 544/296; 544/333; 544/335; 544/357; 544/370; 546/278; 548/125; 548/131; 548/215; 548/240; 548/336; 548/342; 548/347

[58] Field of Search ..... 544/114, 333, 122, 335, 544/295, 370, 296; 546/278; 548/125, 240, 131, 342, 215, 347

[56] References Cited

U.S. PATENT DOCUMENTS 4,122,263 10/1978 Hagen et al. ..... 544/296

*Primary Examiner*—Donald G. Daus
*Assistant Examiner*—James H. Turnipseed
*Attorney, Agent, or Firm*—Keil & Weinkauf

[57] ABSTRACT

Production of new 2-(o-alkylthiophenyl)-1,3-diazacycloalkene hydrohalides by reaction of a benzo-thietane-2-spiro-2'-(1',3'-diazacycloalkane) with an alkyl halide, and the new 2-(o-alkylthiophenyl)-1,3-diazacycloalkene hydrohalides which are pharmaceuticals, auxiliaries for the textile and rubber industries, plant protection agents and starting materials for the production of pharmaceuticals, plant protection agents and dyes.

7 Claims, No Drawings

PRODUCTION OF 2-(O-ALKYLTHIOPHENYL)-1,3-DIAZOCYCLOALKENE HYDROHALIDES

Matter enclosed in heavy brackets [ ] appears in the original patent but forms no part of this reissue specification; matter printed in italics indicates the additions made by reissue.

This application is a continuation-in-part application of Ser. No. 349,915, filed Apr. 11, 1973, now abandoned.

The invention relates to a process for the production of new 2-(o-alkylthiophenyl)-1,3-diazacycloalkene hydrohalides by reaction of a benzothietane-2-spiro-2'-(1',3'-diazacycloalkane) with an alkyl halide.

It is an object of this invention to provide a new process for preparing new 2-(o-alkylthiophenyl)-1,3-diazacycloalkene hydrohalides in good yields and purity.

Another object of this invention is the new 2-(o-alkylthiophenyl)-1,3-diazacycloalkene hydrohalides themselves.

We have found that a 2-(o-alkylthiophenyl)-1,3-diazacycloalkene hydrohalides of the general formula (I):

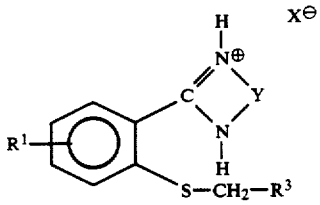

(I)

in which $R^1$ is hydrogen, halogen or an aliphatic radical;

Y is the radical

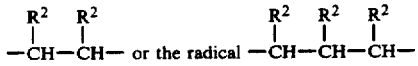

in which the individual radicals $R^2$ may be identical or different and each is hydrogen or an aliphatic radical, $R^3$ is hydrogen or an aliphatic, cycloaliphatic, araliphatic, aromatic, or heterocyclic radical, and X is halogen is obtained advantageously by reacting a benzothietane-2-spiro-2'-(1',3'-diazacycloalkane) of the general formula (II):

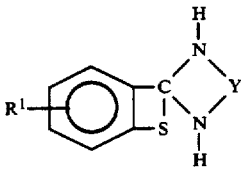

(II)

in which $R^1$ and Y have the meanings given above with an alkyl halide of the general formula (III):

X—CH—$R^3$TM (III)

in which $R^3$ and X have the meanings given above.

When benzothietane-2-spiro-2'-imidazolidine and benzyl chloride are used the reaction of the invention may be represented by the following equation:

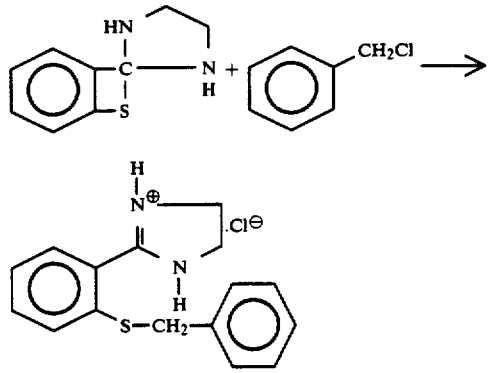

The process of the invention gives the new 2-(o-alkylthiophenyl)-1,3-diazacycloalkene halides in a good yield and high purity.

The starting material (II) is conveniently reacted with the starting material (III) in stoichiometric proportions. Starting material (III) may however be used in excess, for example an excess of up to 1.2 times the stoichiometric amount based on starting material (II). The starting material (II) may be prepared for example by the method described in German published Application No. 2,034,987 laid open Jan. 20, 1972 (see also U.S. Pat. No. 3,776,870) by reaction of a halobenzaldehyde compound with a diaminoalkane and sulfur.

Preferred starting materials (II) and (III) and consequently preferred end products (I) are those in whose formulae $R^1$ is hydrogen, bromo, iodo, chloro or alkyl of one to seven carbon atoms, Y is the radical

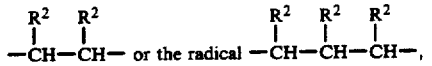

the individual radicals $R^2$ may be identical or different and each is hydrogen or alkyl of one to four carbon atoms, $R^3$ is hydrogen, alkyl of one to seven carbon atoms, alkenyl or alkynyl of two to seven carbon atoms, cyclohexyl, aralkyl of seven to twelve carbon atoms, phenyl or a heterocyclic five-membered or six-membered ring containing one or two nitrogen atoms and/or an oxygen atom and bearing as a substituent alkyl of one to four carbon atoms, aralkyl of seven to 12 carbon atoms or phenyl and X is bromo, iodo or chloro. The heterocyclic ring may bear, as a substituent, another five-membered or six-membered heterocyclic ring containing one or two nitrogen atoms and/or an oxygen atom. They are preferably 1,2,3-oxadiazoles, 1,2,5-oxadiazoles, 1,2,4-oxadiazoles and 1,3,4-oxadiazoles. The said radicals and rings may also bear groups which are inert under the reaction conditions, for example alkyl groups, alkoxy groups in each case of one to four carbon atoms, chloro or bromo as substituents on the phenyl radical.

Examples of starting materials (II) are:

benzothietane-2-spiro-2'-imidazolidine,
benzothietane-2-spiro-(4'-ethylimidazolidine),
benzothietane-2-spiro-(4'-isobutylimidazolidine),
benzothietane-2-spiro-(4',5'-dimethylimidazolidine), benzothietane-2-spiro-(1',3'-diazacyclohexane), benzothientane-2-spiro(1',3'-diaza-4',6'-diethylcyclohexane) and corresponding 3-chlorobenzo-(1,2)-thietane, 5-chloro-(1,2-)-thietane, 3bromobenzo-(1,2)-thietane, 4-chlorobenzo-(1,2)-thietane, 3-methylbenzo-(1,2)-thietane and 4-isobutylbenzo-(1,2)-thietane compounds.

Examples of alkyl halides suitable as starting materials (III) are as follows: ethyl chloride, propyl chloride, hexyl chloride, benzyl chloride, o-chlorobenzyl chloride, m-chlorobenzyl chloride, p-chlorobenzyl chloride, isopropenyl chloride, methyl chloride, allylchloride, propargyl chloride, methallyl chloride, phenylethyl chloride, o,p-dichlorobenzyl chloride, o,o'-dichlorobenzyl chloride, o,m-dichlorobenzyl chloride, p-methoxybenzyl chloride, m-butoxybenzyl chloride, cyclohexyl chloride, pyrryl-(2)-methyl chloride, imidazolyl-(2) methyl chloride, pyridinyl-(2) methyl chloride, morpholinyl-(2)-methyl chloride, oxazolyl-(5)-methyl chloride, furfuryl-(2)-methyl chloride, piperazinyl-(2)-methyl chloride, pyrimidinyl-(b 6)-methyl chloride; 5-chloromethyl-1,2,4-oxadiazole, 5-chloromethyl-3-m-tolyl-1,2,4-oxadiazole, 5-chloromethyl-3-ethyl-1,2,4-oxadiazole, 5-chloromethyl-3-methyl-1,2,4-oxadiazole, 5-chloromethyl-3-p-toluyl-1,2,4-oxadiazole, 5-chloromethyl-3-pyridyl-1,2,4-oxiadiazole, 5-chloromethyl-3-m-chloro-p-toluyl-1,2,4-oxidiazole, 3-o-chlorophenyl-5-chloromethyl-1,2,4-oxadiazole, 3-m-chloromethyl-5-chloromethyl-1,2,4-oxiadiazole, 3-p-chloromethyl-5-chloromethyl-1,2,4-oxadiazole and analogous 5-chloromethyl-1,2,3-oxadiazoles, 4-chloromethyl-1,2,5-oxadiazoles, 3-chloromethyl-1,2,4-oxadiazoles and 5-chloromethyl-1,3,4-oxadiazoles; and corresponding iodides, bromides, bromine compounds and iodine compounds.

The reaction is carried out as a rule at a temperature of from 10° to 150° C., preferably from 50° C. to 100° C., at atmospheric or superatmospheric pressure, continuously or batchwise. It is convenient to use an organic solvent which is inert under the reaction conditions, for example an aromatic hydrocarbon such as benzene or toluene; an alkanol such as methanol, ethanol, propanol or a butanol; a glycol ether such as glycol monomethyl ether or glycol monoethyl ether; or appropriate mixtures. A ratio of from 5 to 20 moles of solvent per mole of starting material (II) is preferred.

The reaction may be carried out as follows: the starting materials (II) and (III), with or without a solvent, are heated to the reaction temperature. The mixture is then allowed to react at the reaction temperature for fron one to five hours. The end product is then separated by a conventional method, for example by crystallization or filtration of the mixture. If necessary the end product may be purified by recrystallization.

The new compounds which can be prepared by the process of the invention are pharmaceuticals, auxiliaries for the textile and rubber industries, plant protection agents and also valuable starting materials for the productions of pharmaceuticals, plant protection agents and dyes. In particular when they are administed perorally or intravenously they cause prolonged increase in blood pressure and affect the central nervous system. They are capable of neutralizing eyelid paralysis in mice caused by reserpin and they increase excretion of urine in rats.

Examples of pharmaceutical properties are given in the following Table. The blood pressure-raising action is detected in the conventional manner on rats narcotized with urethane. Blood pressure is measured from the carotid artery by means of Statham elements. Intravenous injection of the end product (I) is effected through a cannula inserted into the jugular vein. The increase in blood pressure after administration of the test substances is measured in mm of Hg and the duration of action in minutes. The tests are discontinued thirty minutes after administration of the test substance.

The columns in the following Table are as follows:

I = Z

II = $R^3$

III = approximate toxicity in mg/kg administered orally

IV = approximate toxicity in mg/kg administered intravenously

V = maximum increase in blood pressure in mm of Hg after intravenous injection of 1 mg/kg VI = duration of action in minutes VII = remarks.

TABLE

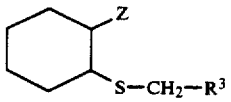

| I | II | III | IV | V | VI | VII |
|---|---|---|---|---|---|---|
| 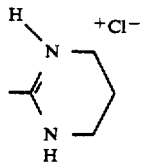 | $-C_6H_5$ | 200 | 30 | 35 | >30 | |
| 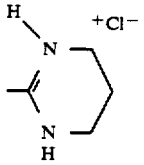 | 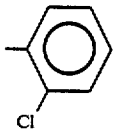 | 200 | 30 | 47 | >30 | |

TABLE-continued

| I | II | III | IV | V | VI | VII |
|---|---|---|---|---|---|---|
| 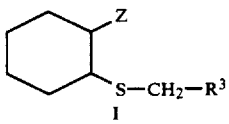 | 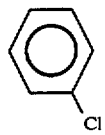 | 100 | 50 | 28 | >30 | |
| 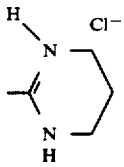 | 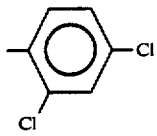 | 100 | 30 | 41 | 8 | |
| 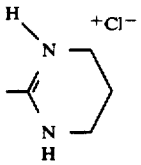 | 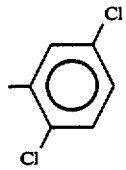 | 200 | 30 | 23 | >30 | |
| 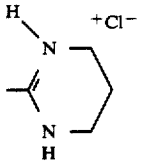 | 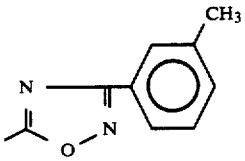 | 200 | 200 | — | — | marked dilation of coronary vessels |
| 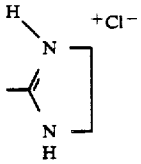 | 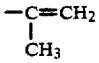 | 100 | 50 | 15 | 26 | |
| 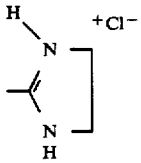 | 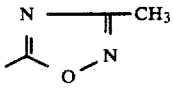 | 200 | 100 | — | — | marked dilation of coronary vessels |

The following Examples illustrate the invention. The parts given in the following Examples are by weight.

EXAMPLE 1

2-(2'-methylthiophenyl)-Δ2-imidazoline hydroiodide

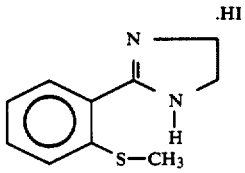

44.5 Parts of benzothietane-2-spiro-2'-imidazolidine is reacted with 35.5 parts of methyl iodide in 400 parts of methanol. The reaction mixture is stirred for three hours at 60° C. and then concentrated to half its volume, cooled and suction filtered. The yield is 68 parts (85% theory) and the melting point is 212° C.

EXAMPLE 2

2-(2'-allylthiophenyl)-Δ2-imidazoline hydrobromide

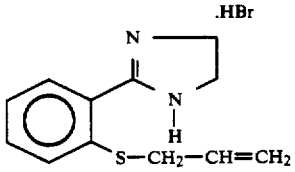

44.5 Parts of benzothietane-2-spiro-2'-imidazolidine is reacted with 30 parts of allyl bromide in 400 parts of methanol. The reaction mixture is stirred for 3 hours at 60° C., then concentrated to half its volume, cooled and suction filtered. The yield is 62 parts (83% of theory) and the melting point is 132° C.

EXAMPLE 3

2-(2'-propargylthiophenyl)-Δ2-imidazoline hydrobromide

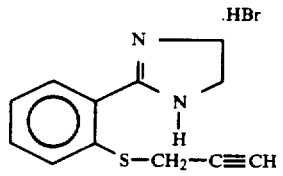

44.5 Parts of benzothietane-2-spiro-2'-imidazolidine is reacted with 30 parts of propargyl bromide in 400 parts of methanol. The reaction mixture is stirred for three hours at 60° C., concentrated, cooled and suction filtered. The yield is 69 parts (93% of theory) and the melting point is 185° C.

EXAMPLE 4

2-(2'-benzylthiophenyl)-Δ2-imidazoline hydrochloride

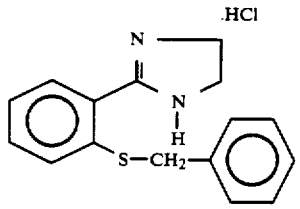

44.5 Parts of benzothientane-2-spiro-2'-imidazolidine is reacted with 31.6 parts of benzyl chloride in 400 parts of methanol. The reaction mixture is stirred for three hours at 60° C., concentrated, cooled and suction filtered. The yield is 64 parts (81% of theory) and the melting point is 217° C.

EXAMPLE 5

2-[2'-(4''-chlorobenzylthio)-phenyl]-Δ2-imidazoline hydrochloride

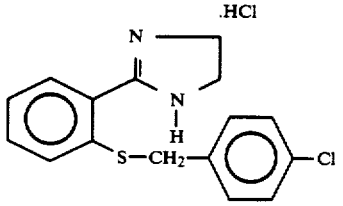

44.5 Parts of benzothientane-2-spiro-2'-imidazolidine is reacted with 40.3 parts of 4-chlorobenzyl chloride in 400 parts of methanol. The reaction mixture is stirred for 3 hours at 60° C., concentrated, cooled aud suction filtered. The yield is 80 parts (94% of theory) and the melting point is 177° C.

EXAMPLE 6

2-[2'-(2''-chlorobenzylthio)-phenyl]-Δ2-imidazoline hydrochloride

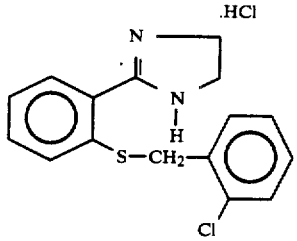

44.5 Parts of benzothientane-2-spiro-2'-imidazolidine is reacted with 40.3 parts of 2-chlorobenzyl chloride in 400 parts of methanol. The reaction mixture is stirred for 3 hours at 60° C., concentrated, cooled and suction filtered. The yield is 67 parts (80% of theory) and the melting point is 202° C.

EXAMPLE 7

2-[2'-(2''-dichlorobenzylthio)-phenyl]-Δ2-imidazoline hydrochloride

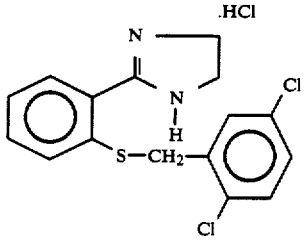

44.5 Parts of benzothientane-2-spiro-2'-imidazolidine is reacted with 49 parts of 2,5-dichlorobenzyl chloride in 400 parts of methanol. The reaction mixture is stirred for three hours at 60° C., concentrated, cooled and suction filtered. The yield is 76 parts (81% of theory) and the melting point is 236° C. (with decomposition).

EXAMPLE 8

2-[2'-(2'',6''-dichlorobenzylthio)-phenyl]-Δ2-imidazoline hydrochloride

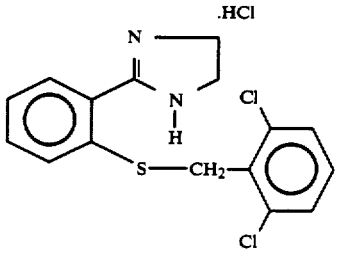

44.5 Parts of benzothietane-2-spiro-2'-imidazolidine is reacted with 49 parts of 2,6-dichlorobenzyl chloride in 400 parts of methanol. The reaction mixture is stirred for 3 hours at 60° C., concentrated, cooled and suction filtered. The yield is 80 parts (86% of theory) and the melting point is 214° C.

EXAMPLE 9

2-[2'-(3''-methyl-1'',2'',4''-oxadizolyl-5''-methylthio)-phenyl]-Δ2-imidazoline hydrochloride

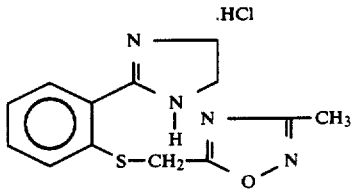

44.5 Parts of benzothietane-2-spiro-2'-imidazolidine is reacted with 33 parts of 3-methyl-5-chloromethyl-1,2,4-oxadiazole in 400 parts of methanol. The reaction mixture is stirred for 3 hours at 60° C., concentrated, cooled and suction filtered. The yield is 58 parts (75% of theory) and the melting point is 225° to 230° C.

EXAMPLE 10

2-(2'-methylthiophenyl)-tetrahydropyrimidine hydroiodide

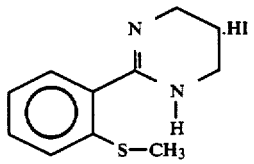

48 Parts of benzothietane-2-spiro-2',1', 3'-diazacyclohexane is reacted with 35.5 parts of methyl iodide in 400 parts of methanol. The reaction mixture is stirred for three hours at 60° C., concentrated, cooled and suction filtered. The yield is 71 parts (85% of theory) and the melting point is 257° C.

EXAMPLE 11

2-(2'-methallylthiophenyl)-tetrahydropyrimidine hydrochloride

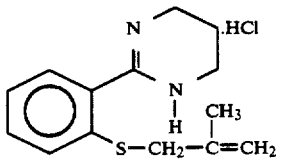

48 Parts of benzothietane-2-spiro-2',1',3'-diazacyclohexane is reacted with 22.6 parts of methallyl chloride in 400 parts of methanol. The reaction mixture is stirred for three hours at 60° C., concentrated, cooled and suction filtered. The yield is 58 parts (82% of theory) and the melting point is 194° C.

EXAMPLE 12

2-(2'-benzylthiophenyl)-tetrahydropyrimidine hydrochloride

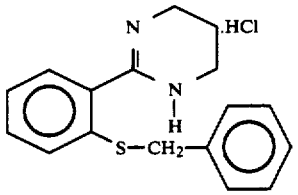

48 Parts of benzothietane-2-spiro-2',1',3'-diazacyclohexane is reacted with 31.6 parts of benzyl chloride in 400 parts of methanol as described in Example 11. The yield is 70 parts (88% of theory) and the melting point is 240° C. with decomposition.

EXAMPLE 13

2-[2'-(2''-chlorobenzylthio)-phenyl]-tetrahydropyrimidine hydrochloride

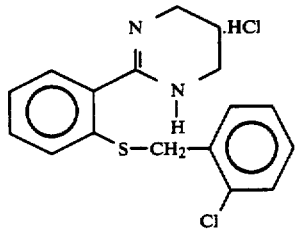

48 Parts of benzothietane-2-spiro-2',1', 3'-diazacyclohexane is reacted with 40 parts of 2-chlorobenzyl chloride in 400 parts of methanol as described in Example 11. The yield is 74 parts (84% of theory) and the melting point is 215° C.

EXAMPLE 14

2-[2'-(3''-chlorobenzylthio)-phenyl]-tetrahydropyrimidine hydrochloride

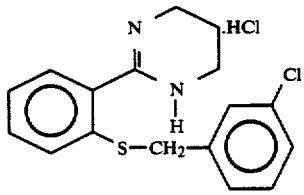

48 parts of benzothietane-2-spiro-2',1',3'-diazacyclohexane is reacted with 40 parts of 3-chlorobenzyl chloride in 400 parts of methanol as described in Example 11. The yield is 76 parts (87% of theory) and the melting point is 224° C.

EXAMPLE 15

2-[2'-(4''-chlorobenzylthio)-phenyl]-tetrahydropyrimidine hydrochloride

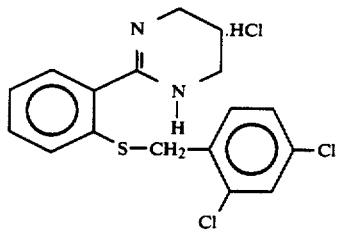

48 Parts of benzothietane-2-spiro-2',1',3'-diazacyclohexane is reacted with 40 parts of 4-chlorobenzyl chloride in 400 parts of methanol as described in Example 11. The yield is 68 parts (77% of theory) and the melting point is 252° C.

EXAMPLE 16

2-[2'-(2'',4''-dichlorobenzylthio)-phenyl]-tetrahydropyrimidine hydrochloride

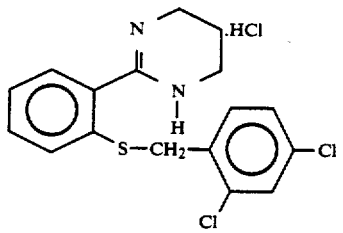

48 Parts of benzothietane-2-spiro-2',1', 3'-diazacyclohexane is reacted with 40 parts of 2,4-dichlorobenzyl chloride in 400 parts of methanol as described in Example 11. The yield is 78 parts (80% of theory) and the melting point is 238° C.

EXAMPLE 17

2-[2'-(2'',5''-dichlorobenzylthio)-phenyl]-tetrahydropyrimidine hydrochloride

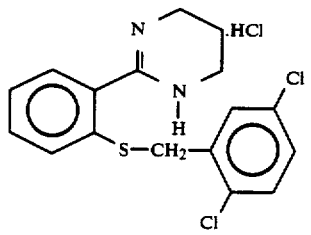

48 Parts of benzothietane-2-spiro-2',1',3'-diazacyclohexane is reacted with 49 parts of 2,5-dichlorobenzyl chloride in 400 parts of methanol as described in Example 11. The yield is 82 parts (85% of theory) and the melting point is 242° C.

EXAMPLE 18

2-[2'-(2'',6''-dichlorobenzylthio)-phenyl]-tetrahydropyrimidine hydrochloride

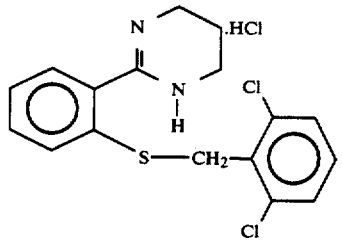

48 Parts of benzothietane-2-spiro-2',1',3'-diazacyclohexane is reacted with 49 parts of 2,6-dichlorobenzyl chloride in 400 parts of methanol as in Example 11. The yield is 74 parts (76% of theory) and the melting point is 250° C.

EXAMPLE 19

2-[2'-(3''-p-methylphenyl-1'',2'',4''-oxadiazolyl-5''-methylthio)-phenyl]-tetrahydropyrimidine hydrochloride

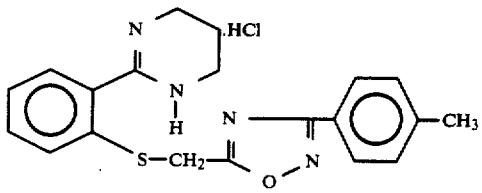

48 Parts of benzothientane-2-spiro-2',1',3'-diazacyclohexane is reacted with 52 prts of 3-p-methylphenyl-5-chloromethyl-1,2,4-oxadiazole in 400 parts of methanol as in Example 11. The yield is 73 parts (73% of theory) and the melting point is 227° to 228° C.

EXAMPLE 20

2-[2'-3''-(3'''-chloro-4'''-methylphenyl)-1'',2'',4''-oxadiazolyl-5''-methylthio-phenyl]-tetrahydropyrimidine hydrochloride

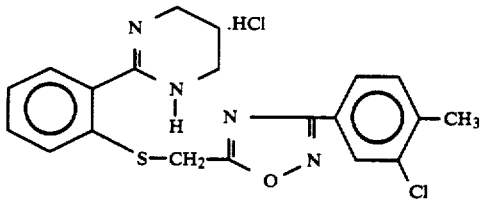

48 Parts of benzothietane-2-spiro-2',1',3'-diazacyclohexane is reacted with 58.6 parts of 3-(3'-chloro-4'-methylphenyl)-5-chloromethyl-1,2,4-oxadiazole in 400 parts of methanol in the manner described in Example 11. The yield is 79 parts (74% of theory) and the melting point is 260° C. with decomposition.

EXAMPLE 21

2-[2'-(3''-m-tolyl-1'',2'',4''oxadiazolyl-5''-methylthio)-phenyl]-tetrahydropyrimidine hydrochloride

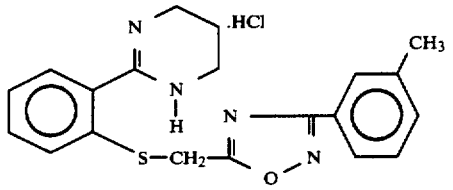

48 Parts of benzothietane-2-spiro-2',1', 3'-diazacyclohexane is reacted with 52 parts of 3-(m-tolyl)-5-chloromethyl-1,2,4-oxadiazole in 400 parts of methanol as described in Example 11. The yield is 61 parts (61% of theory) and the melting point is 232° to 235° C.

EXAMPLE 22

2-[2'-(4''-chlorobenzylthio)-5'-chlorophenyl]-imidazoline hydrochloride

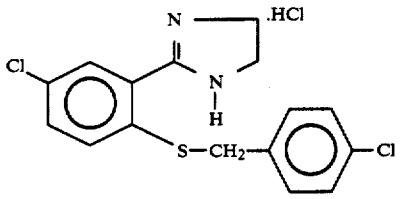

53 Parts of 4-chlorobenzothietane-2-spiro-2'-imidazolidine is reacted with 40 parts of p-chlorobenzyl chloride in 500 parts of methanol as described in Example 11. The yield is 84 parts (91% of theory) and the melting point is 248° to 250° C.).

EXAMPLE 23

2-(2'-methallylthio-5'-chlorophenyl)-imidazoline hydrochloride

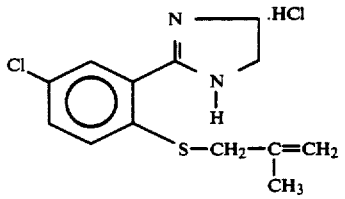

32 Parts of 4-chlorobenzothietane-2-spiro-2'-imidazolidine is reacted in 400 parts of methanol with 13.6 parts of methallyl chloride as described in Example 11. The yield is 42 parts (92% of theory) and the melting point is 228° C.

EXAMPLE 24

2-(2'-benzylthio-5'-chlorophenyl)-imidazolidine hydrochloride

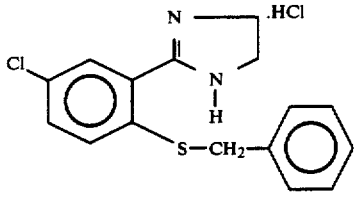

32 parts of 4-chlorobenzothietane-2spiro-2'-imidazolidine is reacted with 19 parts of benzyl chloride in 300 parts of methanol as described in Example 11. The yield is 43 parts (84% of theory) and the melting point is 260° C. with decomposition.

EXAMPLE 25

2-[4'-(2''-chlorobenzylthio)-5'-chlorophenyl]-imidazoline hydrochloride

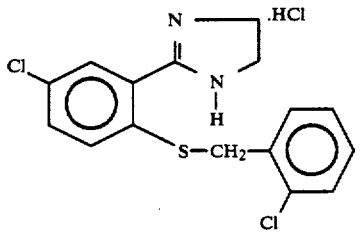

32 Parts of 4-chlorobenzothietane-2-spiro-2'-imidazoline is reacted with 26 parts of 2-chlorobenzyl chloride in 300 parts of methanol. The yield is 52 parts (90% of theory) and the melting point is 260° . with decomposition.

EXAMPLE 26

2-[2'-(3''-chlorobenzylthio)-5'-chlorophenyl]-imidazoline hydrochloride

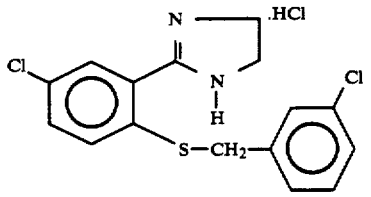

32 Parts of 4-chlorobenzothietane-2-spiro-2'-imidazolidine is reacted with 26 parts of 3-chlorobenzyl chloride in 300 parts of methanol, as described in Example 11. The yield is 49 parts (85% of theory ) and the melting point is 255° C.

EXAMPLE 27

2-[2'-(2'',4''-dichlorobenzylthio)-5'-chlorophenyl]-imidazoline hydrochloride

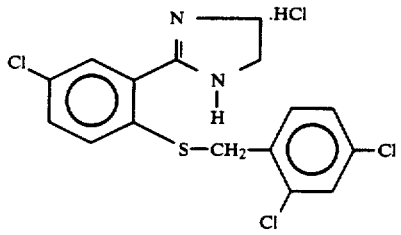

32 Parts of 4-chlorobenzothietane-2-spiro-2'-imidazolidine is reacted in 300 parts of methanol with 29.5 parts of 2,4-dichlorobenzyl chloride in the manner described in Example 11. The yield is 56 parts (90% of theory) and the melting point is 236° C.

EXAMPLE 28

2-[2'-(2'',5''-dichlorobenzylthio)-5'-chlorophenyl]-imidazoline hydrochloride

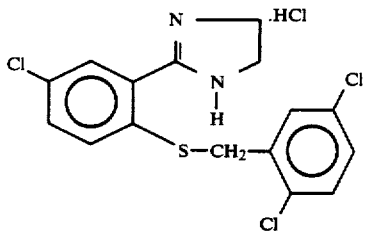

32 Parts of 4-chlorobenzothietane-2-spiro-2'-imidazolidine is reacted as described in Example 11 with 29.5 parts of 2,5-dichlorobenzyl chloride in 300 parts of methanol. The yield is 53 parts (86% of theory) and the melting point is 260° C. with decomposition.

EXAMPLE 29

2-[2'-(3'-methyl-1'',2'',4''-oxadiazolyl-5''-methylthio)-5'-chlorophenyl]-imidazoline hydrochloride

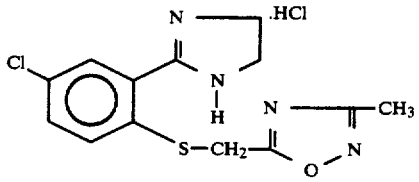

In the manner described in Example 11 53 parts of 4-chlorobenzothietane-2-spiro-2'-imidazolidine is reacted with 33 parts of 3-methyl-5-chloromethyl-1,2,4-oxadiazole in 400 parts of methanol. The yield is 70 parts (81% of theory) and the melting point is 250° to 255° C. with decomposition.

EXAMPLE 30

2-[2'-(3''-p-tolyl-1'',2'',4''-oxadiazolyl-5''-methylthio)-5'-chlorophenyl]imidazoline hydrochloride

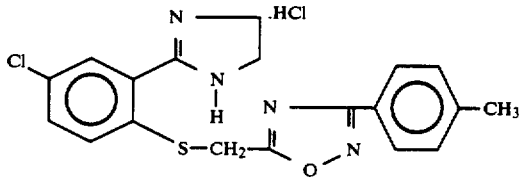

53 Parts of 4-chlorobenzothietane-2-spiro-2'-imidazolidine is reacted with 52 parts of 2-(4'-methylphenyl)-5-chloromethyl-1,2,4-oxidiazole as described in Example 11. The yield is 82 parts (78% of theory) and the melting point is 270° C. with decomposition.

EXAMPLE 31

2-[2'-(3'-(o-chlorophenyl)-1,'',2'',4''-oxadiazolyl-5''-methylthio)-5' chlorophenyl]-imidazoline hydrochloride

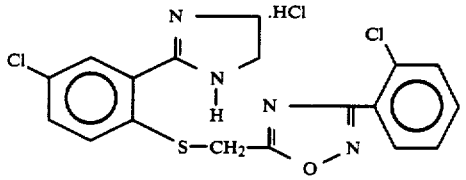

53 Parts of 4-chlorobenzothietane-2-spiro-2'-imidazolidine is reacted with 56 parts of 3-(o-chlorophenyl)-5-chloromethyl-1,2,4-oxadiazole in 400 parts of methanol as described in Example 11. The yield is 96 parts (88% of theory) and the melting point is 265° to 270° C.

EXAMPLE 32

2-[2'-(3'''-chloro-4'''-methylphenyl)-1'',2'',4''-oxadiazolyl-5''-methylthio)-5'-chlorophenyl]-imidazoline hydrochloride:

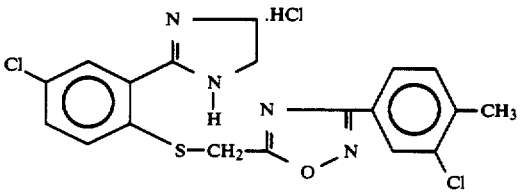

53 Parts of 4-chlorobenzothietane-2-spiro-2'-imidazolidine is reacted with 58.6 parts of 3-(3'-chloro-4'-methylphenyl)-5-chloromethyl-1,2,4-oxadiazole in 400 parts of methanol as described in Example 11. The yield is 89 parts (80% of theory) and the melting point is 260° C. with decomposition.

EXAMPLE 33

2-[2'-(5''-methyl-1'',2'',4''-oxadiazolyl-3''-methylthio)-5'-chlorophenyl]-imidazoline hydrochloride

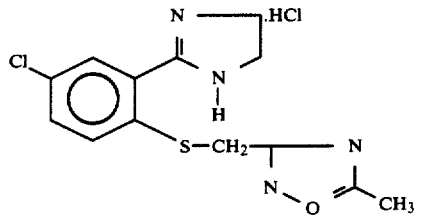

24 Parts of 4-chlorobenzothietane-2-spiro-2'-imidazolidine is reacted in 200 parts of methanol with 15 parts of 3-chloromethyl-5-methyl-1,2,4-oxadiazole as described in Example 11. The yield is 32 parts (82% of theory) and the melting point is 213° to 215° C.

EXAMPLE 34

2-[2'-(2''-p-methoxyphenyl-1'',3'',4''-oxadiazolyl-5''-methylthio)-5'-chlorophenyl]-imidazoline hydrochloride

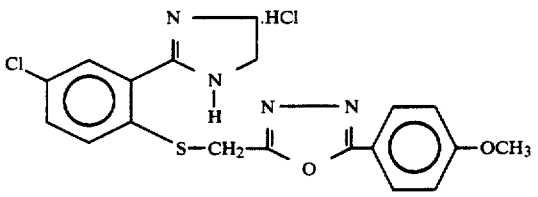

10.6 Parts of 4-chlorobenzothietane-2-spiro-2'-imidazolidine is reacted in 200 parts of methanol with 11.2 parts of 2-p-methoxyphenyl-5-chloromethyl-1,3,4-oxadiazole as described in Example 11. The yield is 18 parts (83% of theory) and the melting point is 272° C.

EXAMPLE 35

2-[2'-(2''-(2''',5'''-dichlorophenyl)-1'',3'',4''-oxadiazolyl-5''-methylthio)-5'-chlorophenyl]-imidazoline hydrochloride

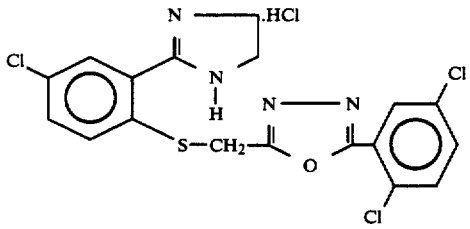

21.2 parts of 4- chlorobenzothietane-2-spiro-2'-imidazolidine is reacted in 500 parts of methanol with 26.3 parts of 2-(2', 5'-dichlorophenyl)-5- chloromethyl-1,3,4-oxadiazole as described in Example 11. The yield is 41 parts (86% of theory) and the melting point is 328° to 330° C.

EXAMPLE 36

2-[2'-(3''-ethyl-1'',2'',4''-oxadiazolyl-5''-methylthio)-5'-chlorophenyl]-imidazoline hydrochloride

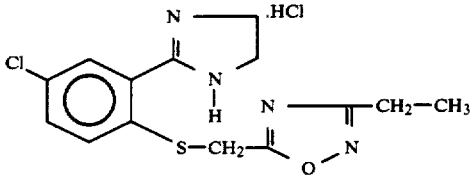

10.6 Parts of 4-chlorobenzothietane-2-spiro-2'-imidazolidine is reacted in 200 parts of methanol with 7.3 parts of 3-ethyl-5-chloromethyl-1,2,4-oxadiazole as described in Example 11. The yield is 15 parts (84% of theory) and the melting point is 120° to 122° C.

EXAMPLE 37

2-[2'-(3''-pyridyl-1'',2'',4''-oxadiazolyl-5''-methylthio)-phenyl]-imidazoline hydrochloride

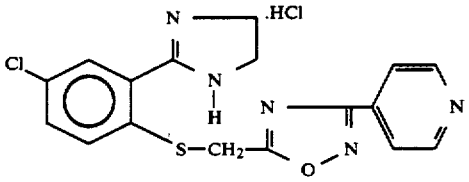

18 Parts of benzothietane-2-spiro-2'-imidazolidine is reacted with 20 parts of 3-pyridyl-5-chloromethyl-1,2,4-oxadiazole in 400 parts of methanol as described in Example 11. The yield is 30 parts (79% of theory) and the melting point is 268° to 270° C.

EXAMPLE 38

2-[2'-(1'',2'',4''-oxadiazolyl-5''-methylthio)-phenyl]-Δ2-imidazoline hydrochloride

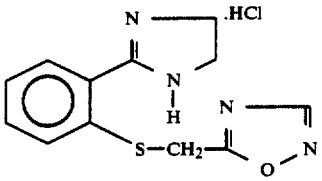

44.5 Parts of benzothietane-2spiro-2'-imidazolidine is reacted with 29.6 parts of 5-chloromethyl-1,2,4-oxadiazole in 400 parts of methanol. The reaction mixture is stirred for 3 hours at 60° C., concentrated, cooled and suction filtered. The yield is 61 parts (82% of theory) and the melting point is 238° to 240 ° C.

The invention is hereby claimed as follows:

1. A process for the production of a 2-(o-alkylthiophenyl)-1,3-diazacycloalkene hydrohalide of the formula

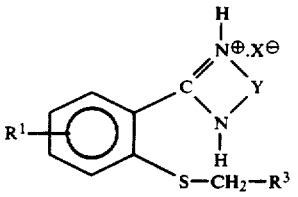

(I)

in which $R^1$ is hydrogen, bromo, iodo, chloro or alkyl of one to seven carbon atoms, Y is the divalent radical $$-\overset{R^2}{\overset{|}{C}}H-\overset{R^2}{\overset{|}{C}}H- \text{ or } -\overset{R^2}{\overset{|}{C}}H-\overset{R^2}{\overset{|}{C}}H-\overset{R^2}{\overset{|}{C}}H$$

wherein each $R^2$ is hydrogen or alkyl of one to four carbon atoms, $R^3$ is hydrogen, alkyl of one to seven carbon atoms, alkenyl or alkynyl of two to seven carbon atoms each, cyclohexyl, aralkyl of seven to twelve carbon atoms, phenyl or a heterocyclic member selected from the group consisting of pyrryl-(2); imidazolyl-(2); pyridinyl-(2); morpholinyl-(2); oxazolyl-(5); furfuryl-(2); piperazinyl-(2); pyrimidinyl-(6); 1,2,3-oxadiazolyl-(4) or -(5), 1,2,4-oxadiazolyl-(3) or -(5), or 1,2,5-oxadiazolyl-(3) or -(4), and the same oxadiazolyl rings substituted once by methyl, ethyl, phenyl or pyridyl; with the proviso that phenyl may further bear an inert substituent selected from the group consisting of alkyl of 1 to 4 carbon atoms, alkoxy of 1 to 4 carbon atoms, chloro or bromo, and X is bromo, iodo or chloro, which comprises: reacting a benzothietane-2-spiro-2'-(1',3'-diazacycloalkane) of the formula

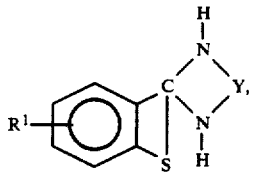

(II)

in which $R^1$ and Y have the meanings given above, with an alkyl halide of the formula:

$$X-CH_2-R^3 \quad \text{(III)}$$

in which $R^3$ and X have the meanings given above, at a temperature of from 10° to 150° C.

2. A process as claimed in claim 1 wherein the reaction is carried out in the presence of an inert organic solvent.

3. A process as claimed in claim 2 wherein said inert organic solvent is selected from the group consisting of aromatic hydrocarbons, alkanols, glycol ethers or mixtures thereof.

4. A process as claimed in claim 3 wherein said solvent is benzene or toluene.

5. A process as claimed in claim 3 wherein said solvent is methanol, ethanol, propanol or butanol.

6. A process as claimed in claim 3 wherein said solvent is glycol monomethyl ether or glycol monoethyl ether.

7. A process as claimed in claim 3 wherein said solvent is methanol.

* * * * *